United States Patent [19]

Fleisher et al.

[11] Patent Number: 5,401,169
[45] Date of Patent: Mar. 28, 1995

[54] MULTIPLE-PART DENTAL MATERIAL DELIVERY SYSTEM

[75] Inventors: Larry D. Fleisher, Maplewood; Thomas W. Martin, Little Canada, both of Minn.

[73] Assignee: Minnesota Mining and Manufacturing, St. Paul, Minn.

[21] Appl. No.: 193,802

[22] Filed: Feb. 9, 1994

Related U.S. Application Data

[63] Continuation-in-part of Ser. No. 75,150, Jun. 10, 1993, abandoned.

[51] Int. Cl.$^6$ ............................................. A61C 5/04
[52] U.S. Cl. ............................................. 433/90
[58] Field of Search ............... 433/80, 82, 83, 87, 433/88, 89, 90; 206/63.5, 524.4, 524.5, 524.6

[56] References Cited

U.S. PATENT DOCUMENTS

| | | | |
|---|---|---|---|
| 3,323,682 | 6/1967 | Creighton, Jr. et al. | 222/94 |
| 4,340,154 | 7/1982 | VanManen | 222/94 |
| 4,386,717 | 6/1983 | Koob | 222/94 |
| 4,391,590 | 7/1983 | Dougherty | 433/90 |
| 4,552,266 | 11/1985 | Weissenburger | 206/220 |
| 4,657,959 | 4/1987 | Bryan et al. | 524/266 |
| 4,676,657 | 6/1987 | Botrie | 366/177 |
| 4,869,400 | 9/1989 | Jacobs | 222/137 |
| 5,082,147 | 1/1992 | Jacobs | 222/137 |
| 5,100,320 | 3/1992 | Martin et al. | 433/90 |
| 5,129,825 | 7/1992 | Discko, Jr. | 433/90 |
| 5,172,807 | 12/1992 | Dragan et al. | 206/219 |

*Primary Examiner*—Gene Mancene
*Assistant Examiner*—Lucchesii Nicholas D.
*Attorney, Agent, or Firm*—Gary L. Griswold; Walter N. Kirn; Dale A. Bjorkman

[57] ABSTRACT

A cartridge for delivery of multiple-part dental materials comprising a) a cartridge body made from an injection moldable material comprising polyalkylene oxide homopolymer or polyalkylene oxide copolymer wherein said homopolymer or copolymer comprises a repeat unit that is

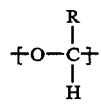

wherein R is H or an aliphatic moiety. The cartridge body has a Burst Pressure greater than that of an otherwise identical cartridge made entirely of polypropylene, and a flexural modulus greater than $1.3 \times 10^3$ MPa at 50% relative humidity and 23° C., and b) a multiple-part dental material. The cartridge is specially adapted to be mounted in a hand-held ejector-type gun.

15 Claims, 1 Drawing Sheet

MULTIPLE-PART DENTAL MATERIAL DELIVERY SYSTEM

This application is a continuation-in-part of U.S. Ser. No. 08/075,150, filed Jun. 10, 1993, now abandoned.

FIELD OF THE INVENTION

The present invention relates to delivery systems for multiple-part dental materials. More particularly, this invention relates to cartridge bodies for delivery of multiple-part dental materials using hand-held ejector-type dispensers, and especially silicone dental impression materials.

BACKGROUND OF THE INVENTION

Hand-held ejector-type dispensing systems have long been used for delivery of multiple-part silicone dental impression materials. The standard in the industry has heretofore been use of polypropylene as the material of choice for manufacture of the cartridge body.

Multiple-part hydrophilic silicones for use in dental impression taking are disclosed, for example, in U.S. Pat No. 4,657,959 to Bryan et. al. Devices useful for delivery of such materials include multiple barrel dispensing devices having a static mixer provided to efficiently mix the separate components as they are extruded from the barrels of the device. An example of such a device is described in U.S. Pat. No. 4,538,920 to Drake.

U.S. Pat. No. 5,100,320 discloses a cartridge for delivery of dental compositions. The material from which the cartridge is manufactured must have a burst strength greater than that of an otherwise identical cartridge made entirely of polypropylene and a 24 hour water absorption less than nylon-6. These materials are discussed at column 4, lines 3–12.

SUMMARY OF THE INVENTION

Multiple-part dental materials present particular challenges in delivery systems because by design each part of the material before mixing has a comparatively low viscosity to allow easy expressing from the cartridge. Upon mixing of the separate parts, viscosity of the composition increases, with subsequent setting of the material. Cartridge bodies containing these multiple part materials can experience significant stresses if the user pauses long enough in the process of expressing the material to allow viscosity changes to occur in the dental material being delivered. Material that has already been mixed at the exit port of the cartridge body may begin to set, creating a viscosity gradient approximating a plugged container. Additionally, recent advances in the technology relating to the hand-held ejector-type gun have increased the amount of force that the user can apply to the cartridge. To specifically address these problems and also to provide superior performance characteristics for multiple-part dental material delivery systems, a cartridge has been developed for such delivery systems, and particularly for delivery of multiple-part dental impression materials. This cartridge comprises a) a cartridge body made from an injection moldable material comprising a polymer selected from the group consisting of polyalkylene oxide homopolymers and polyalkylene oxide copolymers wherein said homopolymer or copolymer comprises a repeat unit that is

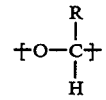

wherein R is selected from the group consisting of H and an aliphatic moiety said cartridge body having a Burst Pressure greater than that of an otherwise identical cartridge made entirely of polypropylene, and wherein the material of the cartridge body has a flexural modulus greater than $1.3 \times 10^3$ MPa at 50% relative humidity and 23° C., said cartridge body comprising a plurality of separate chambers adapted for holding separate parts of a multiple-part dental material and simultaneously dispensing same; and b) a multiple-part dental material contained within said separate chambers of said cartridge body.

The cartridge is specially adapted to be mounted in a hand-held ejector-type gun.

BRIEF DESCRIPTION OF DRAWING

A preferred embodiment of the invention is illustrated in the accompanying drawing, in which.

DETAILED DESCRIPTION OF PRESENTLY PREFERRED EMBODIMENTS

Figure 1:
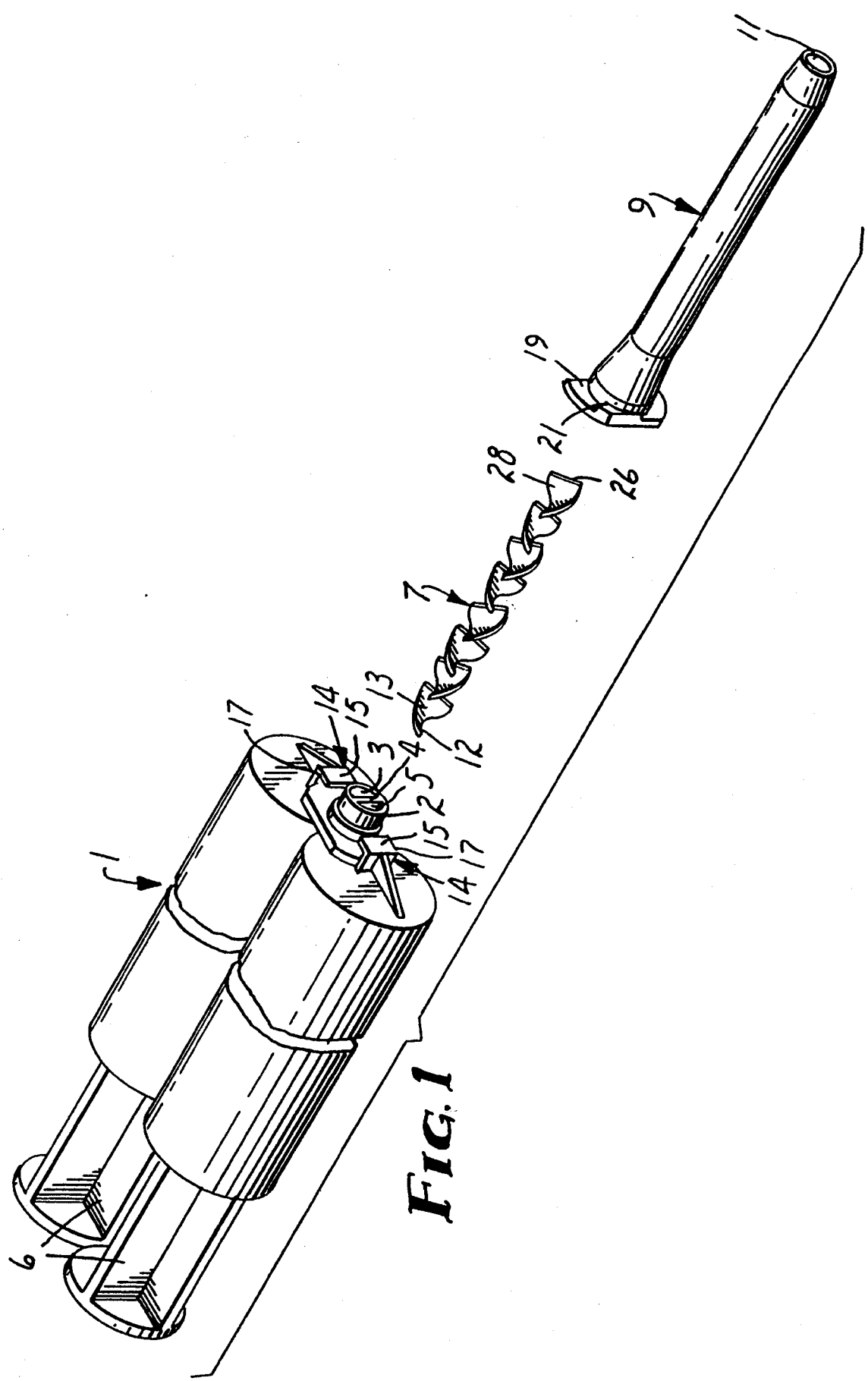
FIG. 1 is an exploded view in perspective of a syringe, static mixing element and exit conduit of this invention.

Previously preferred materials used for making cartridge bodies for dispensing dental materials have been polypropylene and nylons. Polypropylene is dimensionally stable after molding, but is not strong. Certain nylons can be strong, but tend to absorb water, which may adversely affect both strength and dimensional stability. Dimensional stability is particularly important as the size of the cartridge increases and/or as the viscosity of the material contained within the cartridges increases. Thus, for a relatively small capsule such as those used for dispensing of single part dental composites, some warping of the capsule can be tolerated simply because the amount of actual warping is limited due to the size of the capsule. Typical single part dental composite capsules have a volume of less than about one ml. In contrast, typical two-part dental impression material cartridges dispense about 50 ml of material. Upon swelling or warping, the inner diameter of the cartridge may be reduced or the fit between the piston and the cartridge body wall or the cartridge and the nozzle may be adversely affected.

It has been discovered that cartridge bodies made from an injection moldable material comprising a polymer selected from the group consisting of polyalkylene oxide homopolymers and polyalkylene oxide copolymers benefit from the unique combination of properties offered by this class of polymers. Particularly, these materials provide high tensile strength in yield, high impact strength, high flexural modulus, low water absorption, low coefficient of friction, high fatigue resistance and excellent compatibility with the dental material to be delivered therefrom. Because these materials are stiffer in flexure, the cartridge body wall experiences less deflection as the plunger traverses the chamber. Thus, there is less likelihood for dental material to "blow by" the piston and/or the o-ring assembly. A cartridge body is compatible when the dental material can be stored within the cartridge body made from the identified materials for long periods of time with little or no adverse effect on the material properties of the dental materials contained therein. For example, two-part dental impression materials can be stored in the inventive cartridges without adversely affecting the set time of the material upon mixing.

Cartridge bodies according to the present invention are made from an injection moldable material comprising a polymer selected from the group consisting of polyalkylene oxide homopolymers and polyalkylene oxide copolymers wherein said homopolymer or copolymer comprises a repeat unit that is

wherein R is selected from the group consisting of H and an aliphatic moiety. Preferably, R is H or a C1-4 alkyl moiety.

The injection moldable material may also optionally be a polyalkylene oxide copolymer comprising
a) a repeat unit that is

wherein R is selected from the group consisting of H and an aliphatic moiety, and.
b) a repeat unit that is

wherein R' is selected from the group consisting of a straight aliphatic moiety, a branched aliphatic moiety, and a cyclic aliphatic moiety.

Alternatively, the injection moldable material is a blend of a) a polymer selected from the group consisting of polyalkylene oxide homopolymers and polyalkylene oxide copolymers wherein said homopolymer or copolymer comprises a repeat unit that is

wherein R is selected from the group consisting of H and an aliphatic moiety, and b) a second polymer that is compatible with the polymer of section a).

A preferred polymer for manufacture of cartridge bodies of the present invention consists essentially of a homopolymer having methyleneoxy repeating units or a copolymer having methyleneoxy and ethyleneoxy repeating units. More preferably, the polymer primarily consists of methyleneoxy repeating units. Most preferably, the polymer consists essentially of polymethylene oxide homopolymer. The class of polymer containing primarily the oxymethylene repeating unit is trivially known as acetals, and is commercially available from a number of sources. Preferred materials include the Delrin TM polymers from E.I. dupont de Nemours & Co., such as Delrin TM 900, 500 and 500T resins.

A polymeric material from which a cartridge of the invention is made can also comprise a reinforcing filler. Suitable reinforcing fillers include carbon fiber, mica, calcium carbonate, talc, polytetrafluoroethylene, glass (e.g., chopped glass, continuous glass fiber), aluminum flake, mixtures thereof, and the like.

The particular amount of a reinforcing filler that can be used with a material varies from filler to filler and from material to material. Therefore, it is impractical to recite a particular range of filler levels suitable to all fillers and all polymeric materials. In general, however, a filled material can comprise about 10 percent to about 60 percent, preferably 20 percent to about 50 percent, by weight reinforcing filler based on the total weight of the filled material.

Transparent materials can be made opaque by coating (e.g., painting or covering with a label) or preferably by incorporating pigments such as titanium dioxide and carbon black, or colorants (e.g., pigments and/or dyes) in order to prevent light from reaching the dental composition contained therein. Colorants can be incorporated into the material according to well known methods, e.g., as disclosed in the *Modern Plastics Encyclopedia*, Vol. 65, No. 11, pp. 148–150, McGraw-Hill New York (1988).

The cartridge body has a Burst Pressure greater than that of an otherwise identical cartridge made entirely of polypropylene, and the material of the cartridge body comprises polyalkylene oxide homopolymer or copolymer and has a flexural modulus greater than $1.3 \times 10^3$ MPa at 50% relative humidity and 23° C. More preferably, the cartridge body is made from a material having a flexural modulus greater than $1.7 \times 10^3$ MPa, and most preferably a flexural modulus greater than $2.0 \times 10^3$ MPa. The particular polypropylene used in the above-discussed comparison should be an available polypropylene exhibiting the greatest tensile strength with retention of sufficiently high impact strength and flexural modulus. The flexural modulus must be sufficiently high to prevent "blow-by" of the dental material, and the impact strength must be sufficiently high such that the cartridge is not so brittle that it breaks when dropped during handling. Polypropylenes can be obtained with tensile strengths approaching those of the acetals of this invention, which allow more pressure to be put on a cartridge body before it bursts. However, polypropylenes that have tensile strengths in the range suitable for use in cartridge bodies exhibit impact strengths that decrease to unacceptable levels.

Factors other than the selection of the material can affect the structural integrity of the cartridge body. For example, the particular configuration of the cartridge can cause inherent structural weakness. Further, in an injection-molded cartridge, less than optimal mold gating can cause the formation of weak weld lines in the resultant cartridge. Also, the material can become oriented such that a cartridge will be strong along one axis and weak along another.

A cartridge of the invention is preferably relatively small, and is intended to contain an amount of a dental composition that can be substantially fully expended during the course of a single procedure or several (e.g., 2 to about 10) procedures. The volume of the inner chamber (as measured by the volume displaced by the piston's travel) is therefore preferably at least 10 mls of total dental material (i.e. 5 mls for each chamber of a two-part dental material cartridge), and preferably between 30 and 200 mls of total dental material. Most preferably cartridges of the present invention contain between 40 and 60 mls of total dental material.

Wall thickness is such that the cartridge will withstand the pressures exerted during extrusion of a dental composition at a useful rate without bursting or excessive yielding. Preferred wall thickness will vary based on several factors, such as the viscosity of the dental composition, the tensile strength of the material from which a cartridge is made, the dimensions of the inner chamber (e.g., length, shape, and cross-sectional area), and the size of the orifice in the discharge nipple.

Referring now to FIG. 1, there is shown an exploded view in perspective of a cartridge of this invention having a static mixing device located thereon. Syringe 1 has two parallel internal chambers, each of which is intended to be filled with one part of a two-part crosslinkable dental material. The chambers in syringe 1 are separated by barrier 4. When a pair of plungers 6 are forced into the chambers in syringe 1, the contents of the syringe exit via outlet 2 through outlet passages 3 and 5, flow through static mixing element 7 and exit conduit 9, and are intimately mixed to form a homogeneous mass which will crosslink following expulsion from outlet 11 of exit conduit 9. Static mixing element 7 is prevented from being expelled during use from the outlet end of exit conduit 9 by a suitable constriction in the inside diameter of exit conduit 9 proximate its outlet end.

Maximum efficiency of mixing is obtained by ensuring that the inlet end 12 of the first mixing blade 13 of static mixing element 7 is generally perpendicular to the plain of contiguity between the two resin streams exiting syringe 1 through exit passages 3 and 5. Such perpendicular orientation is obtained using a locating tang in exit conduit 9, which locating tang serves to orient static mixing element 7 with respect to syringe 1.

Rotational alignment of exit conduit 9 with respect to syringe 1 is obtained using a suitable mounting means (e.g., a bayonet mount). Bayonet locking tabs 14 have locking prongs 15 and stop surfaces 17. Exit conduit 9 has locking ramps 19 and stop surfaces 21. Exit conduit 9 is mounted on syringe 1 by centering the inlet of exit conduit 9 over outlet 2 of syringe 1, while aligning exit conduit 9 so that it can be pushed between bayonet locking tabs 14. Exit conduit 9 is then inserted firmly over outlet 2, and rotated approximately 90° clockwise (as viewed from the exit end of the conduit) so that locking ramps 19 are wedged between locking prongs 15 and the main body of syringe 1, and stop surfaces 17 engage stop surfaces 21.

When so mounted, exit conduit 9 is fixably rotationally aligned with respect to syringe 1. In addition, through locating means, static mixing element 7 is fixably rotationally aligned with respect to exit conduit 7 and syringe 1. Static mixing element 7 and exit conduit 9 are firmly attached to syringe 1, but can be readily removed and discarded after use by rotating exit conduit 9 approximately 90° counterclockwise (as viewed from the exit end of the conduit) and pulling exit conduit 9 away from syringe 1.

It is possible to directly measure the strength of a cartridge of the invention by employing the Burst Pressure Test described in detail below.

BURST PRESSURE TEST

The discharge end of a cartridge is plugged in any appropriate manner such that the plug remains in place during the test. About one-half of each of the inner chambers of the cartridge is then filled with uncured Express TM Silicone dental impression material (commercially available from 3M). The pistons are placed in the open end of the body. The cartridge is then placed in an Instron TM Model 1123 tensile testing machine operated at a crosshead speed of 100 mm/min. The pistons are displaced by the tensile testing machine toward the discharge end until the cartridge fails by bursting. The force required to cause such failure is measured, and the average of five independent determinations is recorded as an average force. A pressure is calculated by dividing this measured average force measured by the cross-sectional area of the cartridge pistons.

As noted above, a cartridge of the invention exhibits a Burst Pressure greater than that of an otherwise identical cartridge made entirely of polypropylene. More preferably, a cartridge of the invention exhibits a Burst Pressure more than about two times greater than that of an otherwise identical cartridge made entirely of polypropylene. Put in actual numerical terms, a cartridge of the invention exhibits a Burst Pressure of at least about 2.2 MPa, more preferably at least about 3.1 MPa and most preferably at least about 4.0 MPa.

FLEXURAL MODULUS

The Flexural Modulus of a material is determined according to ASTM test D 790, wherein the test is carried out at 50% relative humidity and 23° C.

The Flexural Modulus is greater than $1.3 \times 10^3$ MPa. More preferably, the Flexural Modulus is greater than $1.7 \times 10^3$ MPa, and most preferably greater than $2.0 \times 10^3$ MPa.

The impression material contained within the cartridge body disclosed in the present invention is a multiple-part composition cured by the presence of moisture, crosslinking agents, catalysts and/or heat. Most preferred are two-part addition cure or condensation cure compositions of the room temperature vulcanizing variety. The composition contains a curable silicone prepolymer, that is, a polysiloxane having one or more functional groups which enable the prepolymer to be polymerized or cured to a state of high molecular weight. Suitable silicone prepolymers are well known in the art and are described, for example, in "Silicones" *Kirk-Othmer Encyclopedia of Chemical Technology*, 3rd ed., 20, 922–962 (1982).

Epoxy dental model materials can be contained within the cartridge body of the invention. These materials are used for making replica models of teeth for extraoral use and include those materials disclosed in U.S. Pat. Nos. 4,454,875 and 4,943,237, incorporated herein by reference.

EXPERIMENTAL

Identical cartridges were made of commercially available acetals according to the invention (duPont Delrin 500T and 900, BASF N2640Z2 and Celcon TX 90 acetals) as well as polypropylene SB 912 (available from Himont U.S.A., Inc.). Burst pressure and flexural modulus tests were then performed on five samples of each material as detailed in the preceding sections. Polypropylene SB 912 was chosen as a comparison because it is believed to be the strongest available polypropylene that also possesses the other necessary physical properties of adequate flexural modulus and impact strength to function as a cartridge body for dental materials.

What is claimed:

1. A cartridge for delivery of multiple-part dental materials, said cartridge comprising
   a) a cartridge body made from an injection moldable material comprising a polymer selected from the group consisting of a polyalkylene oxide homopolymer and a polyalkylene oxide copolymer wherein said homopolymer or copolymer comprises a repeat unit that is

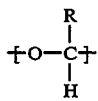

wherein R is selected from the group consisting of H and an aliphatic moiety, said cartridge body having a Burst Pressure greater than that of an otherwise identical cartridge made entirely of polypropylene, and wherein the material of the cartridge body has a flexural modulus greater than $1.3 \times 10^3$ MPa at 50% relative humidity and 23° C., said cartridge body comprising a plurality of separate chambers adapted for holding separate parts of a multiple-part dental material and simultaneously dispensing same; and
   b) a multiple-part dental material contained within said separate chambers of said cartridge body; wherein said cartridge is specially adapted to be mounted in a hand-held ejector-type gun.

2. The cartridge of claim 1, wherein said multiple-part dental material is a silicone dental impression material.

3. The cartridge of claim 1, wherein said multiple-part dental material is an epoxy dental model material.

4. The cartridge of claim 1, wherein said injection moldable material is a polyalkylene oxide homopolymer.

5. The cartridge of claim 4, wherein R is selected from the group consisting of H and C1–C4 alkyl.

6. The cartridge of claim 1, wherein said polymer is a polyalkylene oxide copolymer wherein R further comprises a repeat unit that is

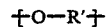

wherein R' is selected from the group consisting of a straight aliphatic moiety, a branch aliphatic moiety, and a cyclic aliphatic moiety.

7. The cartridge of claim 1, wherein said polymer further comprises a second polymer that is compatible with said homopolymer or copolymer.

8. The cartridge of claim 1, wherein said polyalkylene oxide homopolymer consists essentially of polymethylene oxide homopolymer.

9. The cartridge of claim 1, wherein said polyalkylene oxide copolymer consists essentially of methyleneoxy and ethyleneoxy repeat units.

10. The cartridge of claim 1, wherein said cartridge body is made from a material having a flexural modulus greater than $1.7 \times 10^3$ MPa.

11. The cartridge of claim 1, wherein said cartridge body is made from a material having a flexural modulus greater than $2.0 \times 10^3$ MPa.

12. The cartridge of claim 1, wherein said cartridge body has a Burst Pressure about two times greater than that of an otherwise identical cartridge made entirely of polypropylene.

13. The cartridge of claim 1, wherein said cartridge body has a Burst Pressure of at least about 2.2 MPa.

14. The cartridge of claim 1, wherein said cartridge body has a Burst Pressure of at least about 3.1 MPa.

15. The cartridge of claim 1, wherein said cartridge body has a Burst Pressure of at least about 4.0 MPa.

* * * * *